(12) United States Patent
Wantling et al.

(10) Patent No.: US 7,563,826 B2
(45) Date of Patent: *Jul. 21, 2009

(54) EMULSIONS FOR LIGNOCELLULOSIC PRODUCTS, METHODS OF THEIR MANUFACTURE, IMPROVED LIGNOCELLULOSIC PRODUCTS AND METHODS FOR THEIR MANUFACTURE

(75) Inventors: Steven Wantling, Brandon, MS (US); Bonnie S. Zepka, Louisville, KY (US)

(73) Assignee: Hexion Specialty Chemicals, Inc., Columbus, OH (US)

( * ) Notice: Subject to any disclaimer, the term of this patent is extended or adjusted under 35 U.S.C. 154(b) by 537 days.

This patent is subject to a terminal disclaimer.

(21) Appl. No.: 10/541,804

(22) PCT Filed: May 20, 2004

(86) PCT No.: PCT/US2004/016039

§ 371 (c)(1),
(2), (4) Date: Jul. 7, 2005

(87) PCT Pub. No.: WO2005/039841

PCT Pub. Date: May 6, 2005

(65) Prior Publication Data

US 2006/0243323 A1 Nov. 2, 2006

Related U.S. Application Data

(60) Provisional application No. 60/475,922, filed on Jun. 5, 2003, provisional application No. 60/516,937, filed on Nov. 3, 2003.

(51) Int. Cl.
*B01F 3/06* (2006.01)
*C08L 1/02* (2006.01)
*C08L 91/06* (2006.01)
*C09J 101/00* (2006.01)
*C09J 191/06* (2006.01)
*C04B 24/02* (2006.01)
*C04B 24/00* (2006.01)
*C04B 16/00* (2006.01)

(52) U.S. Cl. .......... 516/41; 516/38; 106/18.29; 106/162.1; 106/162.5; 106/164.3; 106/164.4; 106/164.41

(58) Field of Classification Search .......... 516/38, 516/41; 106/162.1, 162.5, 164.3, 164.4, 106/164.41, 166.5, 18.29
See application file for complete search history.

(56) References Cited

U.S. PATENT DOCUMENTS

| | | | |
|---|---|---|---|
| 3,416,933 A | 12/1968 | Nicholson et al. | 106/15 |
| 4,055,433 A | 10/1977 | Morones | 106/10 |
| 4,497,919 A | 2/1985 | Varga et al. | 524/10 |
| 4,681,910 A | 7/1987 | Crockatt et al. | 524/487 |
| 5,120,355 A * | 6/1992 | Imai | 106/2 |
| 5,972,094 A * | 10/1999 | Bates et al. | 106/145.1 |
| 6,165,261 A | 12/2000 | Wantling | 106/778 |
| 6,428,902 B1 | 8/2002 | Amundson et al. | 428/532 |
| 6,663,707 B2 | 12/2003 | Wantling et al. | 106/778 |
| 7,294,189 B2 * | 11/2007 | Wantling | 106/164.3 |
| 2003/0084825 A1 | 5/2003 | Wantling et al. | 106/772 |

FOREIGN PATENT DOCUMENTS

WO  WO 2004/108625 A1  12/2004

* cited by examiner

Primary Examiner—Daniel S Metzmaier (57) ABSTRACT

Emulsions are provided which are useful in imparting water-resistance to lignocellulosic products. In one embodiment, the emulsions contain a nonsaponifiable wax, a saponified wax, an alkyl phenol component, a dispersant/surfactant such as a salt of polynaphthalenesulfonic acid, and a carboxymethylcellulose. Such emulsions may be added to hot, even boiling, water without the emulsion separating of curdling. Various embodiments are stable for extended periods of time when stored at room temperature, do not require the addition of a preservative biocide to avoid contributing to biodegradation in a lignocellulosic product. The emulsions are pourable liquids at room temperature. Optionally, the emulsions may be added to lignocellulosic products with a preservative to inhibit the preservative from leaching out.

13 Claims, 1 Drawing Sheet

EMULSIONS FOR LIGNOCELLULOSIC PRODUCTS, METHODS OF THEIR MANUFACTURE, IMPROVED LIGNOCELLULOSIC PRODUCTS AND METHODS FOR THEIR MANUFACTURE

CROSS-REFERENCE TO RELATED APPLICATIONS

This application was filed under 35 U.S.C. 371 based on PCT/US04/16039, filed 20 May 2004, which claims benefit to provisional applications 60/475,922, filed 5 Jun. 2003, and 60/516,937, filed 3 Nov. 2003.

FIELD OF THE INVENTION

The present invention relates to emulsions useful in improving lignocellulosic composite products and wood. The present invention further relates to a method of making the emulsions.

BACKGROUND OF THE INVENTION

The panel board industry, includes, but is not limited to, plywood, OSB (Oriented Strand Board) (commonly referred to as flake or wafer board), medium density fiber board, particleboard, and other products, inclusively referred to herein as lignocellulosic composite products. In each of these composite products and in lumber (the wood of trees cut and prepared for use as building material) (collectively referred to herein as "lignocellulosic products") it is desirable to control the water absorption or "uptake" and swelling, both of which have detrimental affect on the utility of the product. For example, in plywood used for floor underlay, swelling causes buckling or creep in the final wood or tile overlay. Similar problems occur with swelled OSB used as a roofing member applied to areas which will experience moisture. These composite board panels, like wood and other lignocellulosic products, are also known to deteriorate on the job site due to open storage, as a result of water uptake, which leads to biological degradation resulting from the growth of, and infestation by, bacteria, fungi, and insects.

Lignocellulosic composite products are conventionally manufactured by hot pressing lignocellulosic materials with wax and thermosetting resin. This is referred to as a conventional bonding process. The wax is a sizing agent to improve the water resistance of the composite. The resin is a bonding agent that holds the materials comprising the composite together, thus forming them into a unitary shape. Resoles are commonly used as the binding resin for lignocellulosic composite products.

In the conventional hot press method of manufacture of lignocellulosic composite products, a lignocellulosic material is combined with a phenolic resin and other components in a blender or mixer. The blend or mixture that results is pressed, typically under pressures above atmospheric and temperatures greater than room temperature, to produce the composite. Lignocellulosic materials used in the production of mats may be selected from the group consisting of wood fiber, wood flake, wood strands, wood chips and wood particles, and mixtures thereof. The lignocellulosic materials listed here are referred to in the art as wood furnish. However, it is well known that other wood furnish, such as straw, bagasse, wood bark, recycled wood fiber, recycled paper fiber, and mixtures thereof, may also be used. The wood furnish, once blended or mixed with the phenolic resin, is then formed onto a support material to make a pre-form in the approximate shape of the finished good. The pre-form is then placed on a caul plater in a hot press where the finished good is produced by applying pressures above atmospheric and temperatures greater than room temperature. The elevated temperatures and pressures cause the phenolic resin to polymerize, thus binding the pre-form into a unitary finished good. The hot press method is further described in U.S. Pat. No. 4,433,120 to Shui-Tung Chiu.

Lignocellulosic composite products primarily find use in construction or fabrication. These products may be used in building construction or any fabrication where wood is traditionally used. The poor dimensional stability of state-of-the-art lignocellulosic composite products affects their mechanical properties and reduces their load carrying ability. Another result of poor dimensional stability is unevenness of roof and floor underlayments, and of building siding. Two methods have been principally suggested as means to produce dimensionally stable lignocellulosic composite products. However, both of these methods have proven to be too costly to be used in practice. The first method is referred to as Bulking Treatment. In this method, lignocellulosic materials are impregnated with water-soluble polymers such as polyethylene glycol or impregnated with a low molecular weight resin such as phenol-formaldehyde, or with vinyl monomers and polymerized in situ. The second method is referred to as Chemical Modification. In this method, the lignocellulose may be esterified by, for example, acetylation, or it may be cross-linked using, for example, an aldehyde. An alternative method of Chemical Modification is to react hemicellulose with lignin under elevated temperatures, typically using steam treatment. These methods of chemical modification are costly and reduce the strength of the once-formed composite.

The phenol-formaldehyde resin used in the manufacture of lignocellulosic composite products may be in the form of a solid or a liquid. Powdered phenolic resins, such as novolac, resole, or combinations thereof, may generally be used. U.S. Pat. No. 4,098,770 to Berchem, et al., discloses a spray-dried phenol-formaldehyde resin modified with added non-phenolic polyhydroxy compounds, used in the manufacture of waferboard. Liquid phenol-formaldehyde resins, such as resole or resole and novolac combinations, may also be used in the manufacture of lignocellulosic composite products. Parameters for the manufacture of either liquid or solid phenol-formaldehyde resins are disclosed in *Phenolic Resins, Chemistry, Applications and Performance*, (A. Knop and I. A. Pilato, Springer-Verlag (1985)) and *Advance Wood Adhesives Technology*, (A Pizzi, Marcel Dekker (1994)).

Historically, molten hydrocarbon and simple emulsions utilizing stearic acid/triethanolamine (TEA) or diethanolamine (DEA) and/or lignosulfonate as surfactants have been used in the manufacture of board panels to impact water resistance with varying degrees of performance. However, they generate undesired emissions, inconsistent performance, handling and storage difficulties, foaming, and non-predictable application levels of the wax system to achieve the results.

A method widely used in the conventional bonding process to improve dimensional stability, as noted above, is the application of a wax sizing agent. The wax sizing imparts a certain degree of water repellency to the once-formed composite. Paraffin is a compound sizing agent. One method by which wax sizing imparts water repellency is by coating the surface of the lignocellulose, thus decreasing its surface tension. Another method by which wax sizing imparts water repellency is by partially filling the capillaries within the lignocellulose, thus providing a barrier to the capillary uptake of water.

Conventional preservatives for lignocellulosic products often contain heavy metals, for example, chromated copper arsenate (CCA). Pressure treatment of wood products, i.e., lumber, using CCA is referred to as wolmanizing. Other methods involve the use of creosote oil containing polycyclic aromatic hydrocarbons (PAHs), referred to as creosoting. In these conventional methods, the preservative will often penetrate the wood only around the edges. In addition, the use of a wolmanized and/or creosoted wood is coming under increasing pressure from environmental groups. Problems with CCA-treated wood include difficulty in meeting the Water Pollution Control Laws, the problem of waste wood treated with CCA or the like, at least in part due to the heavy metals present in this preservative. While creosote oil has good permeability, weather resistance and preservative property, it has problems such as odor, skin irritation, health damage, and a black color. Alternative preservative systems for lumber, with lower perceived risk, such as ammoniacal copper quat (ACQ), ammonial copper zinc arsenate (ACZA), copper bis(dimethyldithiocarbamate) (CDDC), ammoniacal copper citrate and copper azole, are also in limited commercial use.

Modern organic biocides are considered to be relatively environmentally benign and not expected to pose the problems associated with CCA-treated lumber, for example. Biocides such as tebuconazole are quite soluble in common organic solvents while others such as chlorothalonil possess only low solubility. The solubility of organic biocides affects the markets for which the biocide-treated wood products are appropriate. Biocides with good solubility can be dissolved at high concentrations in a small amount of organic solvents, and that solution can be dispersed in water with appropriate emulsifiers to produce an aqueous emulsion. The emulsion can be used in conventional pressure treatments for lumber and wood treated in such a manner can be used in products such as decking where the treated wood will come into contact with humans. Biocides, which possess low solubility, are often incorporated into wood in a solution of hydrocarbon oil such as AWPA P9 Type A, and the resulting organic solution is used to treat wood directly. Wood treated in this way can be used only for industrial applications, such as utility poles and railway ties, because the oil is irritating to human skin.

There is a need for lignocellulosic products that are dimensionally stable when exposed to moisture. There is a further need for lignocellulosic products that do not swell when immersed in water and that do not shrink when dried, and there is a need for applying a broad range of preservatives and organic biocides to wood and lignocellulosic composite products.

SUMMARY OF THE INVENTION

In one embodiment, an emulsion described herein comprises a nonsaponifiable wax, a saponified wax, an alkyl phenol component, a dispersant/surfactant, a carboxymethylcellulose component, and water. In a particular embodiment, the nonsaponifiable wax may comprise about 33% to about 35% of the emulsion, by weight, the saponified wax may comprise about 3% to about 5% of the emulsion, by weight, the alkyl phenol component may comprise about 0.5% to about 2.5% of the emulsion, by weight, the dispersant may comprise about 0.5% to about 2% of the emulsion, by weight, and the carboxymethylcellulose component may comprise about 0.2% to about 5% of the emulsion, by weight. Optionally, the emulsions may comprise a preservative.

A method for improving the water resistance of a lignocellulosic composite product prepared by mixing lignocellulosic material with a binder to form a mixture and solidifying the mixture in a selected configuration to form the composite product comprises adding to the mixture an emulsion as described above. A lignocellulosic composite product may be made by mixing lignocellulosic material with a binder to form a mixture, adding to the mixture an emulsion as described above, and solidifying the mixture in a selected configuration to form the composite product. A method for treating wood comprises impregnating the wood with an emulsion as described above.

A method is also provided for making an emulsion, the method comprising charging a single vessel with a molten nonsaponifiable wax, a molten saponified wax, an alkyl phenol component, water, a dispersant/surfactant, and a carboxymethylcellulose component to form a mixture, and heating and agitating the mixture in the vessel. The mixture may then be homogenized. Preferably, the method may include providing saponified wax by charging the vessel with molten saponifiable wax and a saponifier.

A method is also provided for adding preservative to lignocellulosic product, comprising impregnating the lignocellulosic product with a preservative solution comprising the preservative and an emulsion in a carrier solvent, and removing carrier solvent from the lignocellulosic product. In one embodiment, impregnating the lignocellulosic product comprises placing the lignocellulosic product in a chamber, depressurizing the chamber, adding the preservative solution to the chamber in contact with the lignocellulosic product and re-pressurizing the chamber.

Also disclosed are lignocellulosic products resulting from said method.

DETAILED DESCRIPTION OF THE INVENTION

Emulsions described herein are useful in improving the water resistance of lignocellulosic products, thus ameliorating the detrimental effects that absorbed water can have on such products, including dimensional instability (swelling) and biological degradation. Optionally, these emulsions may include preservatives that are not themselves water-repellant, the emulsions serving as carriers for delivering the preservatives into lignocellulosic products e.g., lumber, and in inhibiting the leaching of such preservatives from such products thereafter.

The emulsions described herein result from the combination of a wax component comprising a nonsaponifiable wax, a saponifiable wax, a saponifier, an alkyl phenol component, a dispersant/surfactant such as a phenate salt, a carboxymethylcellulose, and water, which are formed into an emulsion with the wax component becoming the discontinuous phase. These wax-in-water emulsions may be added to a mixture of lignocellulosic materials, and/or other components that go into the composite products, without adversely affecting properties of the mixture which are necessary to the manufacture of lignocellulosic composite products, and they may be impregnated into lumber. Methods for making and using such emulsions, and lignocellulosic products containing such emulsions are also disclosed.

Examples of lignocellulosic materials from which lignocellulosic composite products may be made using these emulsions include, but are not limited to, wood fiber, wood flake, wood strands, wood chips and wood particles, straw, bagasse, wood bark, recycled wood fiber, recycled paper fiber, and mixtures thereof. The composite panels produced are known as fiberboard, waferboard, strandboard, oriented strandboard, flakeboard, particleboard, plywood and the like. Such products may also contain resins such as phenol-formaldehyde (PF), urea-formaldehyde (UF), or a combination thereof, provided in the furnish from which the products are formed. The emulsions described herein may be mixed with such resins to provide a combined system for delivery to the composite-making process. Without wishing to be bound by any particular theory, it is believed that in these emulsions the surfactant system aligns with the discontinuous phase (i.e., wax phase) and may couple with lignin fibers, providing hydrophobicity to composite products, e.g., boards, containing those fibers.

Emulsions described herein comprise a wax component comprising a nonsaponifiable wax and a saponifiable wax. The nonsaponifiable wax may comprise a wax having a melting point greater than about 120° F. (about 49° C.), e.g., about 120° F. to about 165° F. (about 49° C. to about 74° C.), optionally about 120° F. to about 150° F. (about 49° C. to about 66° C.), and preferably about 135° F. to about 145° F. (about 57° C. to about 63° C.). (All ranges disclosed herein are inclusive and combinable, e.g., ranges of "about 120° to about 165° F., optionally from 135° to 145° F.", are inclusive of the endpoints and all intermediate values of the ranges and combinations thereof, including, e.g., about 120° to about 145° F., about 130° to about 150° F., etc.) Suitable nonsaponifiable waxes include paraffin waxes, slack waxes and scale waxes. Such waxes are commercially known to be of low volatility, exhibiting less than about a 10% loss in weight during standard thermogravimetric analysis. Also, the oil content of these waxes is typically less than about 5% by weight, preferably less than about 1% by weight. Some of these waxes are of a relatively high molecular weight, having an average chain length of $C_{36}$, that is a 36 carbon chain length, or greater. Paraffin waxes are typically derived from light lubricating oil distillates and are predominantly straight chain hydrocarbons having an average chain length of 20 to 30 carbon atoms. Suitable paraffin waxes include Wax 3816 available from Honeywell/Astor of Duluth, Ga. Slack waxes are petroleum waxes having an oil content of 3 to 50 wt %. Suitable slack waxes include Exxon 600 Slack Wax and Ashland 200 Slack Wax, and a combination of 50 parts Exxon 600 Slack Wax and 50 parts Ashland 200 Slack Wax.

A suitable saponifiable wax has an acid value or a saponification value and a melting point greater than about 180° F. (about 82° C.). Saponifiable waxes include waxes from the liquefication of coal, vegetable waxes and oxidized waxes resulting from the processing and/or refining of slack wax, scale wax or crude petroleum. For example, saponifiable waxes include montan wax, carnauba wax, beeswax, bayberry-myrtle wax, candelilla wax, caranday wax, castor bean wax, esparto grass wax, Japan wax, ouricury wax, retamoceri mimbi wax, shellac, spermaceti wax, sugar cane wax, wool-lanolin wax, and others. One example of a useful saponifiable wax is a montan wax having a melt point of about 190° to about 200° F. (about 88° to about 93° C.) melt point. Saponification of such waxes occurs as a result of combining the wax with a saponifier, i.e., strongly basic material such as ammonium hydroxide or an alkali metal hydroxide such as sodium hydroxide or potassium hydroxide. The amount of saponifier needed to saponify a wax may be calculated based on the saponification value of the wax. For example, the saponification value divided by 1000 equals the grams of potassium hydroxide to add per gram of wax.

Preferably, the waxes do not contain more than about 5% (by weight) polar compounds as impurities.

The wax component may be present in an amount of about 25 percent by weight (wt %) to about 50 wt %, based on the total weight of the emulsion, preferably about 30 wt % to about 40 wt %. Preferably, the wax component comprises a combination of a nonsaponifiable wax having a melting point of greater than or equal to about 120° F. and a saponifiable wax. The nonsaponifiable wax may comprise about 25 wt % to about 44 wt % of the total weight of the preservative composition, and the saponifiable wax may comprise about 0.5 wt % to about 5 wt % of the total weight of the emulsion. A preferred combination of waxes is a combination of a paraffin wax such as Honeywell 3816 as the first wax and a saponifiable wax such as montan wax. In one embodiment, the wax component comprises paraffin wax in an amount of about 25 wt % to about 45 wt %, preferably about 30 wt % to about 40 wt %, and saponifiable wax in an amount of about 2.5 wt % to about 5 wt %, preferably about 3.5 wt % to about 4.5 wt %, based on the total weight of the emulsion.

A strongly basic compound is added to the emulsion mixture to saponify the saponifiable wax. The saponifier may comprise, e.g., ammonium hydroxide or an alkali metal hydroxide, e.g., sodium hydroxide or potassium hydroxide. The alkali metal hydroxide may be provided in the form of a concentrated aqueous solution that may comprise about 45% alkali metal hydroxide, by weight. Ammonium hydroxide may be provided in solid form. Some or all of the saponifier may also react with the dispersant, and/or with other component ingredients of the emulsion, in situ. Although ammonium hydroxide is sometimes objected to because of the ammonia odor it produces, ammonium hydroxide is believed to be advantageous because, in addition to saponifying the wax, the ammonia can serve as a scavenger for formaldehyde in the resin with which the emulsion is used, and may thus reduce the emission of formaldehyde from the finished composite product. The combination of ammonium hydroxide with formaldehyde also ameliorates the ammonium hydroxide odor, so in some embodiments, formaldehyde may be added to the emulsion for this purpose, for example, in an amount of about 0.02 to about 0.1% by weight. In addition, ammonium hydroxide is especially advantageous for when the emulsion is used with lignocellulosic materials comprising northern wood species, i.e., Douglas fir, aspen and the like.

The saponifier may be provided in an amount of about 0.15% to about 4.5%, optionally about 0.5% to about 3%, of the emulsion, by weight. Optionally, concentrated aqueous saponifier may be provided in an amount of about 0.5 to about 3% by weight of the emulsion; ammonium hydroxide may be added in solid form in an amount of about 0.15 to about 3% by weight of the emulsion. The amount of saponifier may be varied with the type of saponifiable wax used, or with the type of wood. As a result of the saponifier, an emulsion as described herein may have a pH of about 8.5 to about 12.5, for example, a pH of about 8.5 to about 9.5.

Exemplary carboxymethylcellulose materials useful in these emulsions have molecular carbon chain lengths of about 20 to about 50 carbons. An example of a suitable carboxymethylcellulose is carboxymethylcellulose sodium, available from Penn Carbose, Somerset, Pa., under the trade designation LT-30, which is described as having carbon chain lengths of about 26 to 30 carbons. Other suitable carboxymethylcellulose materials include Penn Carbose LT-20 and LT-42. The carboxymethylcellulose and the product of its reaction with the saponifier or with any other component in the emulsion are referred to herein as the "carboxymethylcellulose component".

A salt of polynaphthalenesulfonic acid is useful in the emulsions described herein and, without wishing to be bound by theory, is believed to act as a dispersant/surfactant. The salt may be the product of an in-situ reaction of polynaphthalenesulfonic acid and a saponifier, e.g., an alkali metal hydroxide. One commercially available polynaphthalenesulfonic acid is DISAL GPS which may be obtained from Handy Chemical, Montreal, Quebec, Canada. The acid and acid salt are referred to collectively as a polynaphthalenesulfonic acid component or, more broadly (to include substitute materials), as the dispersant/surfactant. The dispersant/surfactant may comprise about 0.1% to about 5% of the emulsion, by weight, optionally about 0.25 wt % to about 5 wt %.

Incorporating all alkyl phenol into the emulsions has been found to facilitate achieving low water absorption in the final lignocellulosic composite product. As used herein, "alkyl phenol" refers to a phenolic compound having a long chain alkyl group. The long chain alkyl group may be straight or branched. The long chain alkyl group may be $C_{20}$-$C_{42}$ (from 20 to 42 carbon chain length), e.g., $C_{24}$-$C_{34}$, preferably $C_{24}$-$C_{28}$. Such alkyl phenols include polymerized methylene-coupled alkyl phenol, phenate salts, calcium phenates, long branched chain calcium alkyl phenols, long straight chain calcium alkyl phenols and complex polymers of maleic acid with and without an amine group substitution. The long chain alkyl group may be a polymeric group such as a polyethylene, polypropylene, or polybutylene group, for example. The alkyl substituents may be a mixture of different chain lengths as is often the case with commercially available materials. Preferably, the alkyl phenol is chosen so that the average carbon chain length of the alkyl portion matches, i.e., is approximately the same as or is close to, the average carbon chain length of the carboxymethylcellulose. For example, an alkyl phenol of average chain length in the range of about $C_{24}$ to about $C_{34}$ may be used in an emulsion comprising carboxymethylcellulose having an average chain length of about 26 to about 32 carbons, e.g., Carbose LT-30 carboxymethylcellulose.

The alkyl group of the alkyl phenol can be derived from a corresponding olefin; for example, a $C_{26}$ alkyl group is derived from a $C_{26}$ alkene, preferably a 1-alkene, a $C_{34}$ alkyl group is derived from a $C_{34}$ alkene, and mixed length groups are derived from the corresponding mixture of olefins. When the alkyl group is an alkyl group having at least about 30 carbon atoms, however, it may be an aliphatic group (or a mixture of such groups) made from homo- or interpolymers (e.g., copolymers, terpolymers) of mono- and di-olefins having 2 to 10 carbon atoms, such as ethylene, propylene, butene-1, isobutene, butadiene, isoprene, 1-hexene, and 1-octene. Aliphatic hydrocarbyl groups can also be derived from halogenated (e.g., chlorinated or brominated) analogs of such homo- or interpolymers. Such groups can, however, be derived from other sources, such as monomeric high molecular weight alkenes (e.g., 1-tetracontene) and chlorinated analogs and hydrochlorinated analogs thereof, aliphatic petroleum fractions, particularly paraffin waxes and cracked and chlorinated analogs and hydrochlorinated analogs thereof, white oils, synthetic alkenes such as those produced by the Ziegler-Natta process (e.g., poly(ethylene) greases) and other sources known to those skilled in the art. Unsaturation in the hydrocarbyl groups can be reduced or eliminated, if desired, by hydrogenation according to procedures known in the art. Preparation by methods and materials that are substantially free from chlorine or other halogens is sometimes preferred for environmental reasons.

More than one alkyl group can be present, but usually no more than 2 or 3 are present for each aromatic nucleus in the aromatic group. Most typically only one hydrocarbyl group is present per aromatic moiety, particularly where the hydrocarbyl-substituted phenol is based on a single benzene ring.

The alkyl phenol and product of the reaction of an alkyl phenol with a saponifier or with any other component of the emulsion is referred to herein as the alkyl phenol component.

The amount of alkyl phenol component present in the emulsion is about 0.25 wt % to about 10 wt %, optionally about 0.5 wt % to about 2.5 wt % based on the total weight of the emulsion.

One example of an alkyl phenol component useful in the compositions of the present invention is commercially available under the trade designation 319H from Lubrizol Chem. Corp. Wycliffe, Ohio, which material is described as a $C_{24}$-$C_{34}$ polymerized methylene-coupled alkyl phenol.

A novel method of manufacture for the emulsions described herein results in time, energy, operator, and production efficiencies. The method involves mixing the ingredients of the emulsion in a single vessel and then conveying the mixture of a homogenizer under conditions such as the following. An advantage of this method is that the emulsion mixture is prepared in a single vessel; it is not necessary to prepare and separately store partial mixtures of the ingredients of the emulsion in separate vessels before combining them together.

The nonsaponifiable wax (e.g., 3816 wax, further described below) is melted and stored in molten form, e.g., at about 10° F. above its melt point temperature, and water is provided at a temperature that will not cause the wax to solidify. The vessel is then charged in the following illustrative manner:

a. Charge the melted nonsaponifiable wax, e.g., 3816 wax, at a temperature of about 189° F. to about 192° F. (about 87° C. to about 89° C.);

b. Start heat and agitation;

c. Charge molten saponifiable wax and alkyl phenol with continued agitation;

d. Charge a majority of the water, e.g., 95%, and continue agitation;

e. Charge the dispersant/surfactant, (e.g., DISAL polynaphthalenesulfonic acid, further described elsewhere herein), carboxymethylcellulose and saponifier;

f. Charge the remaining water—preferably including the water used to rinse the tubes calculated and subtracted out of the total;

g. Bring the tank up to temperature, e.g., about 190° F. to about 210° F. (about 88° C. to about 100° C.);

h. Continue to agitate while maintaining temperature for about 30 to about 150 minutes;

i. Put through homogenizer at about 1500 to about 3500 PSI (about 10 megapascals (MPa) to about 24 MPa);

j. Cool, optionally in process that provides two exotherms, including a first exotherm between the exit temperature from the homogenizer to a temperature above ambient, and a second exotherm to ambient (storage) temperature. For example, the emulsion composition is passed from the homogenizer to a cooler to achieve a first exotherm of, e.g., about 10° F. to about 20° F. degrees lower than the homogenizer exit temperature, and then to a cooling tank to achieve a second exotherm of, e.g. about an additional 5° F. to about 15° F. lower, optionally under agitation. In one embodiment, the first exotherm may occur by cooling from about 130° F. to about 110° F., and the second exotherm may occur by cooling from about 110° F. to about 70° F.

Without wishing to be bound by any particular theory, using a two-exotherm cooling process allows a phasing process of the formation of the emulsion to proceed to completion. As a result, the viscosity of the emulsion is more stable over time and the emulsion is more stable when subject to shear agitation than if a single exotherm cooling process is used. In an alternative method of preparing the emulsion, a batch process may be used in which a first premix comprising the molten waxes and alkylphenol may be prepared, and a second premix (an aqueous premix) comprising the water, carboxymethylcellulose and polynaphthalenesulfonic acid and saponifier may be prepared, and the first and second premixes may then be combined in a mixing tank for a time sufficient at least for the waxes to become saponified, e.g., for one to three hours, and the resulting mix may then be passed to a homogenizer and cooled as described above.

Illustrative ranges of ingredients in some embodiments of emulsions described herein are provided in Table 1 below.

TABLE 1

ILLUSTRATIVE EMBODIMENTS

| Component | Typical Amount (% weight basis) |
|---|---|
| Nonsaponifiable Wax | 33-35 |
| Saponifiable Wax | 3-5 |
| Alkyl Phenol | 0.5-2.5 |
| Polynaphthalenesulfonic Acid | 0.5-2 |
| Carboxymethylcellulose | 0.2-5 |
| Saponifier | Amount used depends on amount of saponifiable wax; typically 0.5-3 |
| Water | Balance (to 100) |

Table 2 provides example proportions of ingredients in a specific embodiment of an emulsion as described herein.

TABLE 2

ILLUSTRATIVE EMULSION INCLUDING POLYNAPHTHALENESULFONIC ACID

| Component | Weight % |
|---|---|
| Wax 3816 | 33.00 |
| Saponifiable Wax | 3.00 |
| Alkyl Phenol | 0.50 |
| Polynaphthalenesulfonic Acid (DISAL GPS) | 0.50 |
| Carboxymethylcellulose | 0.2 |
| 45% KOH (saponifier) | 0.75 |
| Water | Balance (to 100) |

The emulsions described herein may include optional additional ingredients to enhance their performance during the manufacture of the lignocellulosic composite products and the performance of the resulting composite products. An emulsion as described herein may have a viscosity of about 10 to about 100 centipoise, measured on a Brookfield viscometer. One sample emulsion had a viscosity of 9 cps at about 40% solids. The stability and shear performance and lack of foam generation further enhance the ability to receive these emulsions. For example, one sample emulsion remained intact even after four minutes agitation in a food blender. These emulsions are also compatible with urea-formaldehyde and phenol-formaldehyde resin systems used in the manufacture of many lignocellulosic products. Further, this system is amphoteric and would therefore be stable over a wide pH range, and becomes a part of the total process rather than additive to the process, thus providing a more uniform finished product. Embodiments of these emulsions have been demonstrated not to contribute to biological activity.

Oriented strand board (OSB) is one type of composite that can be manufactured using an emulsion as described herein. To produce OSB using the hot press method, lignocellulosic material is combined with a resin and the emulsion of the present invention in a mixer. The resulting pre-form mixture is flowed onto a support material to make a pre-form for 7/16 inch (about 1.1 centimeters (cm))- and 5/8 inch (about 1.6 cm)-thick oriented strand board. The pre-form is then placed on a caul plate in a hot press where the finished good is produced by applying pressures above atmospheric and temperatures greater than room temperature. The hot press method is further described in U.S. Pat. No. 4,433,120 to Shui-Tung Chiu. Twelve inch by twelve inch (30.5 cm×30.5 cm) panels can be cut from the finished good and tested for density, swell and absorption. Optionally, the pre-form mixture may include a preservative mentioned below to inhibit unwanted biological growth in the panels.

To illustrate the water-resistance imparted by emulsions described herein, several samples of oriented strand board (OSB) were prepared with varying amounts of an emulsion. Sample OSB boards were prepared from mixtures of wood strands, flakes or wafers with a resin binder and an emulsion as described in Table 2 in amounts ranging from about 1% to about 0.25% on a volume basis of the resin in the mixture ("vol. %"). The mixtures were placed in a mold and cured to yield boards. A comparison board was prepared using 1 vol. % of a commercially available comparative emulsion known as Cascowax EW-58, which is believed to comprise a stearic acid TEA emulsion have a solids content of about 58%. Samples were cut from the boards, were measured and weighed and were then immersed in water at about room temperature (e.g., about 72° F. (about 22° C.)) for 24 hours, after which they were again measured and weighed.

The following Table 3 shows the various charges of sample emulsions, the control, and the results of water absorption, edge swell and thickness swell test results from tests performed. Water absorption was measured as the increase in weight of a sample relative to the starting weight. Edge swell is a measure of the average increase in the thickness of the sample measured along one or more edges, relative to the starting thickness, and center swell is a measure of the increase in thickness of the sample at the center, relative to the starting thickness.

TABLE 3

Twenty-Four-hour water absorption (WA) and Thickness Swell Results

| Sample | Vol % emulsion | % WA | % Edge swell | % Center swell | Density (pcf) |
|---|---|---|---|---|---|
| Control | 1.0% | 73.09 | 40.04 | 36.03 | 44.3 |
| Sample 1 | 1.0%* | 50.34 | 22.53 | 22.32 | 41.9 |
| Sample 2 | 0.75%* | 54.18 | 28.61 | 18.91 | 43.7 |
| Sample 3 | 0.5%* | 52.29 | 25.09 | 21.54 | 41.8 |
| Sample 4 | 0.25%* | 84.92 | 37.57 | 29.47 | 40.1 |

*% volume basis in resin wood (OSB) (oriented strand board)

The data of Table 3 show that the sample emulsion provides significantly improved performance in both water uptake and edge and center swell in wood composite products. Specifically, Samples 1-3 had lower water absorption, edge thickness swell, and center swell than the control, and were all similar to each other, even though samples 2 and 3 contained significantly less emulsion than the control. The data shows that improved performance is achieved at reduced rates on a volume/volume basis relative to the control, i.e., approximately 50-75% less emulsion versus the control. The test emulsions release fewer emissions from OSB and other board products, cause less board/resin interference, and they are less sensitive to storage condition requirements than certain other emulsions. Application was on an equal liquid application, therefore lower solids applied for all wax conditions. To be noted is the slightly higher density of the emulsion wax sample. The reduction in emissions is due, at least in part, to the fact that results comparable to the control may be attained with a charge of emulsions that introduces lesser quantities of materials into the lignocellulosic product. For example, Table 3 shows that better results were obtained with 1% of the sample emulsion, which contains only about 40% solids, than with 1% of the control, which contained about 60% solids. Another factor that may contribute to a reduction in emissions is that the described emulsions comprise higher melting waxes, which contain smaller volatile fractions than lower-melting waxes.

Embodiments of the described emulsions that contain ammonium, e.g., from an ammonium hydroxide saponifier, exhibit superior performance relative to other embodiments. This was demonstrated by preparing a series of emulsions all of which made with the following: 33% nonsaponifiable wax; 3% montan wax, 0.5% alkylphenol; 2% polynaphthalene-sulfonic acid (or, where noted 2.5%); 0.5% carboxymethyl-cellulose. The embodiments were made with the indicated quantity of saponifier, the nonsaponifiable waxes and with additional components in the amount set forth in the following Table 4, with water comprising the balance. The samples of Table 4 were prepared using the batch process described above. In emulsions B and E, the indicated formaldehyde was included in the aqueous premix; in emulsions C, F, G, H, and I, the indicated formaldehyde was added to the emulsion after the emulsion was formed from the other components.

TABLE 4

| Emulsion | Ammonium hydroxide | formaldehyde | Nonsaponifiable wax |
|---|---|---|---|
| A | 0.38% | 0.0 | 3816 |
| B | 0.38% | 0.25 | 3816 |
| C | 0.38% | 0.25 | 3816 |
| D | 0.45% | 0.0 | 3816 |
| E | 0.45% | 0.25 | 3816 |
| F | 0.45% | 0.25 | 3816 |
| G[i] | 0.45% | 0.25 | 3816 |
| H | 0.45% | 0.25 | Prowax[ii] 561 |
| I | 0.45% | 0.25 | Prowax[ii] 321 |
| J | 0.45% | 0.0 | 3816 |

Figure 1:
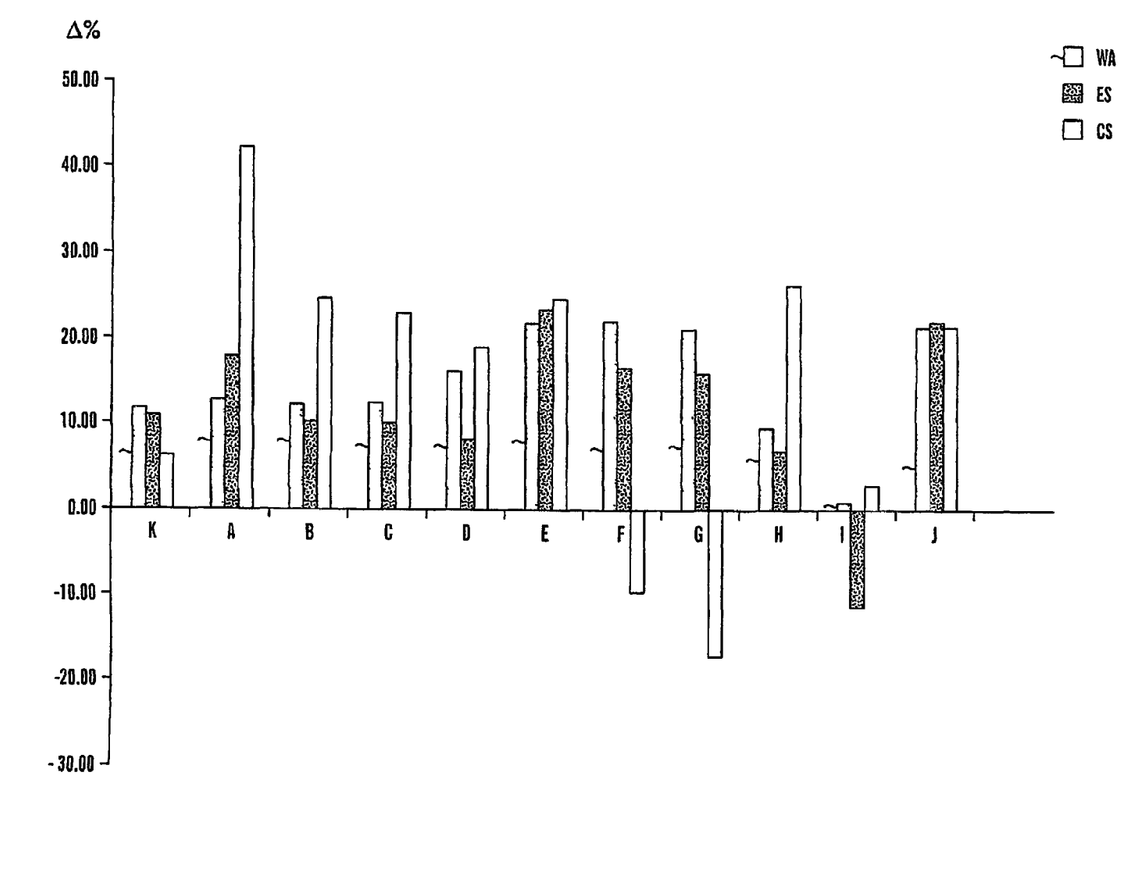
The sole FIGURE is a plot of the test results of sample boards prepared with the disclosed emulsions, in relation to a commercially available control.

[i]Emulsion G contained 2.5% polynaphthalenesulfonic acid
[ii]Prowax 561 and 321 are hard paraffin waxes commercially available from ExxonMobil Corporation Samples of oriented strand board (OSB) were prepared using emulsions A-J. In addition, a sample OSB was prepared using an emulsion as set forth in Table 2 above (designated sample 'K' in the FIGURE), and another sample (whose performance is represented by the base line 0%) was made using a commercially available Cascowax emulsion sold under the commercial designation EW-50S, which is believed to be a paraffin wax emulsion with stearic acid and TEA (triethanolamine). The samples were tested for water absorption, edge swell and center swell as described above. The results are set forth in the accompanying FIGURE, in which the reduction in water absorbance (bars WA), edge swell (bars ES) and center swell (bars CS) of each of the other samples is shown in the FIGURE as a degree of improvement (% Δ) relative to the baseline sample. The results shown in the FIGURE indicate that all of the sample emulsions performed better than the EW-50S in at least two of the three tests.

The experimental results demonstrate that the emulsions described herein provide superior performance with regard to imparting water resistance in lignocellulosic products, and so eliminates the need for lignin compounds and biocides in some of those products. The elimination of these latter two compounds improves the manufacture and lowers cost of the lignocellulosic composite products and wood using these emulsions.

The emulsions described herein can be incorporated into lumber or other lignocellulosic products to help resist the absorption of water. The subsequent drying of the lignocellulosic product is believed to break the emulsion, which releases the waxes therein and allows the waxes to migrate to the surface of the product, thus enhancing the water-resistance characteristics. Optionally, the emulsions described herein can be adjuvants for impregnating preservatives into lignocellulosic composite products or into wood in amounts effective to inhibit a biological activity, i.e., biological degradation, such as the growth of molds, fingi, bacteria, insects, etc. Used in this way, the emulsions help the lignocellulosic material retain the preservatives and reduces the amount of preservatives that leach into the environment when the preserved product is placed in use.

To evaluate the ability of emulsions described herein to help retain absorbed preservatives in lumber or other lignocellulosic products and to prevent the leaching of preservatives therefrom, a copper-based preservative (ACQ) was impregnated into wood samples with a sample emulsion and a comparative emulsion, and the preserved wood samples were then immersed in water and the tendency of the copper to leach out was observed, as follows.

A preservative solution is prepared by combining 25% of a 40% solution of ACQ with 70% water and 5% of a sample emulsion as described in Table 2. The resulting mixture was stirred at room temperature for 2 minutes. The copper concentration in this starting mixture was measured using DSC (differential scanning calorimetry) methods known in the art. A comparative solution was prepared using a comparative stearic acid and triethanolamine composition that is commercially available from Osmose, of Griffin, Ga., USA or Arch-Wood Protection Incorporated of Smyrna, Ga., USA.

Sanded pine wood lath strip specimens measuring 2 inch× ¼ inch×12 inches in length were placed in the wood preservative solution for 2 minutes with vigorous stirring, and were then withdrawn. The amount of copper retained in the solution after each specimen was withdrawn was again measured, and the difference from the starting solution indicated the amount of copper impregnated into the wood specimen.

The specimens were allowed to drip dry for 2 minutes, and were then dried for 24 hours in an oven controlled to 70 degrees F. After drying, each treated wood specimen was immersed in clean water with vigorous stirring for 2 minutes. The quantity of copper in the water was then determined using DSC techniques, and the difference between the amount of copper in the water and the amount absorbed by the specimen was the amount retained by the specimen; the relative amount of copper in the water indicated the degree of leaching.

Results: From the specimens impregnated with a preservative solution comprising the comparative emulsion, about 100% of the impregnated copper leached out, whereas from the specimens impregnated with the preservative solution comprising the sample emulsion, only 15% to about 25% of the impregnated copper leached out. These results show the superiority of the sample emulsions described herein for carrying preservatives into wood and preventing the leaching of the preservatives from the wood thereafter.

Commonly, lumber comprises wood that has been impregnated with a preservative in a process that employs a preservative solution comprising the preservative in a carrier solvent (typically water). The method involves placing the wood in a vacuum chamber, evacuating the chamber, introducing a preservative solution into the chamber in contact with the lumber, pressurizing the chamber to facilitate absorption of the preservative solution by the wood, and then depressurizing the chamber to withdraw carrier solvent from the wood. The preservative is carried into the wood during absorption, and at least a portion of the preservative remains in the wood after carrier solvent is removed. The emulsions described herein can be added to the preservative solution to facilitate absorption of the preservatives by the wood and the retention of the preservatives therein when carrier solvent is subsequently removed.

Suitable preservatives that may be incorporated into lignocellulosic products with an emulsion described herein may be inorganic or organic, and include, for example biocides such as insecticides, fungicides, bactericides, and combinations comprising one or more of the foregoing biocides. The biocide may be chosen according to (1) the target organism; (2) solubility characteristics; (3) stability to the temperature and pH; and other conditions found in the manufacture of the composites. Biocides include substances that kill or inhibit the growth of microorganisms such as molds, slimes, fungi, bacteria, etc. Insecticides, fungicides and bactericides are all examples of biocides. Fungicides include substances that kill or inhibit the growth of fungi. Bactericides include agents that kill bacteria. Insecticides are agents that kill insects. More specific examples of biocides include, but are not limited to, chlorinated hydrocarbons, organometallics, halogen-releasing compounds, metallic salts, organic sulfur compounds, and phenolics. Preferred biocides include but are not limited to chromated copper arsenate (CCA); such as ammoniacal copper quaternary ammonium (ACQ), ammonial copper zinc arsenate (ACZA), copper bis(dimethyldithiocarbamate) (CDDC), ammoniacal copper citrate and copper azole, copper naphthenate, zinc naphthenate, quaternary ammonium salts, pentachlorophenol, tebuconazole (TEB), chlorothalonil (CTL), chlorpyrifos, isothiazolones, propiconazole, other triazoles, pyrethroids, and other insecticides, imidichloprid, oxine copper and the like, and combinations comprising one or more of the foregoing biocides. In addition to the organic biocides, nanoparticles with variable release rates that incorporate such inorganic preservatives as boric acid, sodium borate salts, zinc, zinc borate, silicated borate, copper salts and zinc salts may be used.

Suitable general microbicides include, for example, 3-isothiazolones, 3-iodo-2-propynylbutylcarbamate, 1,2-dibromo-2,4-dicyanobutane, methylene-bis-thio-cyanate (T), 2-thiocyano-methylthiobenzothiazole, tetrachloroisophthalonitrile, 5-bromo-S-nitro-1,3-dioxane, 2-bromo-2-nitropropane-1,3-diol, 2,2-di-bromo-3-nitrilopropionamide (DB-NPA), N,N'-dimethylhydroxyl-5,5'-dimethyl-hydantoin, bromochlorodimethylhydantoin, 1,2-benzisothiazolin-3-one, 4,5-tri-methylene-2-methyl-3-isothiazolone, 5-chloro-2-(2,4-dichlorophenoxy)-phenol, 3,4,4'-trichlorocarbanilide, copper naphthenate, copper-8-hydroxy-quinoline, zinc borate, boric acid, trimethyl boron, zinc oxide, glutaraldehyde, 1,4-bis(bromo-acetoxy)-2-butene, 4,5-dichloro-1,1-dithiacyclopentene-3-one, chlorothalonil, quaternary ammonium based compounds, and combinations comprising one or more of the foregoing microbicides.

Suitable fungicides include, for example, zinc dimethyl dithiocarbamate, 2-methyl-4-t-butylamino-6-cyclopropylamino-s-triazine, 2,4,5,6-tetrachloroisophthalonitrile, N,N-dimethyl dichlorophenyl urea, copper thiocyanate, N-(fluorodichloromethylthio)phthalimide, N,N-dimethyl-N'-phenyl-N-fluorodichloromethylthiosulfamide; copper, sodium and zinc salts of 2-pyridinethiol-1-oxide; tetramethylthiuram disulfide, 2,4,6-trichlorophenyl-maleimide, 2,3,5,6-tetrachloro-4-(methylsulfonyl)-pyridine, diiodomethyl p-tolyl sulfone, phenyl (bispyridil) bismuth dichloride, 2-(4-thiazolyl)-benzimidazole, pyridine triphenyl borane, phenylamides, halopropargyl compounds, propiconazole, cyproconazole, tebuconazole and 2-haloalkoxyaryl-3-isothiazolones (such as 2-(4-trifluoromethoxyphenyl)-3-isothiazolone, 2-(4-trifluoromethoxy-phenyl)-5-chloro-3-isothiazolone, 2-(4-trifluoromethoxyphenyl)-4,5-dichloro-3-isothiazolone), and combinations comprising one or more of the foregoing fungicides.

The fungicide may be an agricultural fungicide such as, for example, dithiocarbamate and derivatives such as ferbam, ziram, maneb (manganese ethylenebisdithio-carbamate), mancozeb, zineb (zinc ethylenebisdithiocarbamate), propineb, metham, thiram, the complex of zineb and polyethylene thiuram disulfide, dazomet, and mixtures of these with copper salts; nitrophenol derivatives such as dinocap, binapacryl and 2-sec-butyl-4,6-dinitrophenyl isopropyl carbonate; heterocyclic structures such as captan folpet, glyodine, dithianon, thioquinox, benomyl, thiabendazole, vinolozolin, iprodione, procymidone, triadimenol, triadimefon, bitertanol, fluoroimide, triarimol, cycloheximide, ethirimol, dodemorph, dimethomorph, thifluzamide and quinomethionate; miscellaneous halogenated fungicides such as: chloranil, dichlone, chloroneb, tricamba, dichloran and polychloronitrobenzenes; fungicidal antibiotics such as: griseofulvin, kasugamycin and streptomycin; miscellaneous fungicides such as diphenyl sulfone, dodine, methoxyl, 1-thiocyano-2, 4-dinitrobenzene, 1-phenyl-thiosemicarbazide, thiophanate-methyl and cymoxanil; acylalanines such as furalaxyl, cyprofuram, ofurace, benalaxyl, and oxadixyl; fluazinam, flumetover, phenylbenzamide derivatives such as those disclosed in EP 578,586-A, amino acid derivatives such as valine derivatives disclosed in EP 550,788-A, methoxyacrylates such as methyl (E)-2-(2-(6-(2-cyanophenoxy)pyrimidin-4-yloxy)phenyl)-3-methoxyacrylate, benzo(1,2,3)thiadiazole-7-carbothioic acid S-methyl ester, propamocarb, imazalil, carbendazim, myclobutanil, fenbu-conazole, tridemorph, pyrazophos, fenarimol, fenpiclonil, pyrimethanil, and combinations comprising one or more of the foregoing fungicides.

Combination bactericides/fungicides can be included in the preservative compositions. An example of a bactericide/fungicide is METASOL D3TA, which is 3,5-dimethyl-tetrahydro-1,3,5,2H-thiadiazine-2-thione available from Ondo-Nalco, Houston, Tex.

Suitable insecticides include, for example, acephate, aldicarb, α-cypermethrin, azinphos-methyl, bifenthrin, binapacryl, buprofezin, carbaryl, carbofuran, cartap, chlorpyrifos, chlorpyrifos methyl, clofentezine, cyfluthrin, cyhexatin, cypermethrin, cyphenothrin, deltamethrin, demeton, demeton-S-methyl, demeton-O-methyl, demeton-S, demeton-S-methyl sulfoxide, demephion-O, demephion-S, dialifor, diazinon, dicofol, dicrotophos, diflubenzuron, dimethoate, dinocap, endosulfan, endothion, esfenvalerate, ethiofencarb, ethion, ethoate-methyl, ethoprop, etrimfos, fenamiphos, fenazaflor, fenbutatin-oxide, fenitrothion, fenoxycarb, fensulfothion, fenthion, fenvalerate, flucycloxuron, flufenoxuron, fluvalinate, fonofos, fosmethilan, furathiocarb, hexythiazox, isazophos, isofenphos, isoxathion, methamidophos, methidathion, methiocarb, methomyl, methyl parathion, mevinphos, mexacarbate, monocrotophos, nicotine, omethoate, oxamyl, parathion, permethrin, phorate, phosalone, phosmet, phosphamidon, pirimicarb, pirimiphos-ethyl, profenofos, promecarb, propargite, pyridaben, resmethrin, rotenone, tebufenozide, temephos, TEPP, terbufos, thiodicarb, tolclofos-methyl, triazamate, triazophos, vamidothion, and combinations comprising one or more of the foregoing insecticides.

Antitermite agents may be used in addition to other insecticides as long as they do not detract from the properties of the other insecticides. Antitermite agents include Permetorin, Imidachlopride, Etpfenplox, and combinations comprising one or more of the foregoing agents.

Specific examples of suitable preservatives include alkylammonium compounds such as didecyldimethylammonium chloride (DDAC), BARDAP (N,N-didecyl-N-methylpolyoxyethylammonium propionate), copper benzalconium chloride or N-alkylbenzyldimethylammonium chloride (BKC); metal salts of naphthetic acid such as copper naphthenate (NCU) or zinc naphthenate (NZN); metal salts of versatic acid such as zinc versatate; triazole type compounds such as Cyproconazole [(2RS,3RS;2RS,3SR)-2-(4-chlorophenyl)-3-(cyclopropyl-1-(1H-1,2,4-triazol-1-yl)butan-2-01], Tebuconazole [(RS)-1-p-chlorophenyl-4,4-dimethyl-3-(1H-1,2,4-triazol-1-ylmethyl)pentan-3-01], Propiconazole [1-[2-(2,4-dichlorophenyl)-4-propyl-1,3-dioxoran-2-ylmethyl]-1H-1,2,4-triazole], 1-[2-(2',4-dichlorophenyl-1,3-dioxoran-2-ylmethyl]-1H-1,2,4-triazol-1-ethanol or 1-[2-(2',4'-dichlorophenyl)-4-propyl-1,3-dioxoran-2-ylmethyl]-1H-1,2,4-triazol-1-ethanol; and organic iodine compounds such as IF-1000[4-chlorophenyl-3-iodopropargyl formal], IPBC [3-iodo-2-propynyl-N-butylcarbamate], and combinations comprising one or more of the foregoing preservatives.

The lignocellulosic preservatives may be used in combination. Preferred combinations include Cyproconazole and DDAC; Cyproconazole and BARDAP; Tebuconazole and Propiconazole; and the like.

A compound which is effective to inhibit or prevent growth of wood rot soil bacteria and wood soft rot fingi, mainly wood soft rot fungi such as *chaetomium globosum*, may also be used as a preservative. Such compounds include p-cumylphenol (PCP), and its salts such as the sodium salt of p-cumylphenol, the ethylamine salt of p-cumylphenol, and combinations comprising one or more of the foregoing wood preservatives. PCP inhibits the growth of wood rot soil bacteria, ascomycetes and inperfect fungi, and it is effective as an antimold agent and antitermite agent. Therefore, PCP is particularly preferable. PCP can exhibit a sufficient effect to wood materials in the treatment amount (application amount) of about 200-1,000 grams per cubic meter of wood ($g/m^3$).

The emulsions described herein may also contain general additives for wood preservatives. For example, petroleum resins, rosins and waxes can reinforce microbicidal activity of preservatives such as PCP and impart sustainability, and therefore are suitable additional additives.

Dinitrophenol, dinitro-o-cresol, chloronitrophenol and the like known as phenol type microbicides of woods do not have antimicrobicidal activity to ascomycetes, and are therefore not included in the wood preservatives of this disclosure.

Mixtures comprising one or more of the foregoing preservatives may also be used. One or more preservatives may be employed in amounts effective to inhibit biological activity in wood or in the lignocellulosic composite product in which it is disposed, e.g., in amounts of about 0.02 wt % to about 1 wt % of an emulsion, preferably about 0.1 wt % to about 1 wt % of an emulsion; such amounts generally result in about 2 to about 120 grams per cubic foot of wood ($g/ft^3$) (about 70 to about 4240 grams per cubic meter ($g/m^3$)) and about 12 to about 120 $g/ft^3$ (about 425 to about 4240 $g/m^3$). For example, the preservative may be present in an amount that imparts about 0.031 pounds of preservative per cubic foot (about 500 $g/m^3$) of wood.

In addition to the lignocellulosic preservatives, it may be desirable to add other additives to the preservative compositions. For example, it may be desirable to treat wood and wood products with fire retarding chemicals such as borax/boric acid, guanylurea phosphate-boric acid, dicyandiamide phosphoric acid formaldehyde, diethyl-N,N-bis(2-hydroxyethyl)-aminomethyl phosphate, and combinations comprising one or more of the foregoing additives. These fire retardants are readily incorporated into nanoparticles formed, for example, from polyvinylpyridine or polyvinylchloride. Other additives that are confer desirable characteristics on wood and wood products and which may be added to the compositions are water repellants, colorants, UV inhibitors, adhesive catalysts, and combinations comprising one or more of the foregoing additives.

There has been disclosed emulsions and lignocellulosic composite products made using such an emulsion. These emulsions are useful in imparting water-resistance to the lignocellulosic composite products and do not contribute to biological activity in the products. In some embodiments, these emulsions may be added to hot, even boiling, water without the emulsion separating or curdling, they may be stable for extended periods of time when stored at room temperature, they may not require the addition of a bactericide, and/or they may be pourable liquids at room temperature. Optionally, these emulsions may contain preservatives. While certain embodiments and best mode are described herein, these embodiments are merely illustrative. It will be apparent to those skilled in the art that modifications may be made therein without departing from the spirit and the scope of the appended claims.

What is claimed is:

1. An emulsion comprising:
   a wax component comprising a nonsaponifiable wax and a saponified wax;
   an alkyl phenol component comprising a $C_{20}$-$C_{42}$ alkyl group;
   a dispersant/surfactant;
   a carboxymethylcellulose component; and
   water.

2. The emulsion of claim 1 wherein the wax component comprises about 25% to about 50% of the emulsion, by weight.

3. The emulsion of claim 1 wherein the nonsaponifiable wax is a slack wax, a scale wax, a paraffin wax or a combination thereof.

4. The emulsion of claim 1 wherein the saponified wax is produced by reaction of a saponifiable wax with ammonium hydroxide, an alkali metal hydroxide or a combination thereof.

5. The emulsion of claim 4 comprising a saponified wax produced by reaction of a saponifiable wax with ammonium hydroxide.

6. The emulsion of claim 1 comprising a saponified wax produced by reaction of a saponifiable wax with potassium hydroxide or sodium hydroxide.

7. The emulsion of claim 6 wherein the wax component comprises about 30% to about 40% of the emulsion, by weight.

8. The emulsion of claim 1 wherein the alkyl phenol component comprises a $C_{24}$-$C_{34}$ alkyl group.

9. The emulsion of claim 1 wherein the alkyl phenol component comprises a $C_{24}$-$C_{28}$ alkyl group.

10. The emulsion of claim 1 wherein the dispersant/surfactant comprises a polynaphthalenesulfonic salt.

11. The emulsion of claim 1 wherein the alkyl phenol component comprises an alkyl phenol having an alkyl group that has an average carbon chain length that matches the carbon chain length of the carboxymethylcellulose.

12. The emulsion of claim 1, wherein the nonsaponifiable wax comprises about 33% to about 35% of the emulsion, by weight;

the saponified wax comprises about 3% to about 5% of the emulsion, by weight;

the alkyl phenol component comprises about 0.5% to about 2.5% of the emulsion, by weight;

the dispersant/surfactant comprises about 0.5% to about 2% of the emulsion, by weight; and the carboxymethylcellulose component comprises about 0.2% to about 5% of the emulsion, by weight.

13. The emulsion of claim 12 wherein the saponified wax is produced by a reaction of a saponifiable wax with ammonium hydroxide, and further comprising about 0.5% formaldehyde, by weight.

* * * * *